United States Patent
Hsiao et al.

(10) Patent No.: US 9,157,057 B2
(45) Date of Patent: Oct. 13, 2015

(54) MONASCUS PURPUREUS MUTANT, NUCLEOTIDE SEQUENCE FOR MONASCUS PURPUREUS MUTANT AND PRIMERS FOR NUCLEOTIDE SEQUENCE OF MONASCUS PURPUREUS MUTANT

(71) Applicants: Hsia-Ching Hsiao, Taipei (TW); Tzu-Ming Pan, Sijhih (TW)

(72) Inventors: Hsia-Ching Hsiao, Taipei (TW); Tzu-Ming Pan, Sijhih (TW)

( * ) Notice: Subject to any disclaimer, the term of this patent is extended or adjusted under 35 U.S.C. 154(b) by 0 days.

(21) Appl. No.: 14/142,814

(22) Filed: Dec. 28, 2013

(65) Prior Publication Data

US 2014/0242675 A1 Aug. 28, 2014

Related U.S. Application Data

(63) Continuation-in-part of application No. 12/946,823, filed on Nov. 15, 2010, now abandoned.

(51) Int. Cl.
*C12N 1/14* (2006.01)
*C12P 17/16* (2006.01)
*C12R 1/645* (2006.01)

(52) U.S. Cl.
CPC .............. *C12N 1/14* (2013.01); *C12P 17/162* (2013.01); *C12R 1/645* (2013.01)

(58) Field of Classification Search
None
See application file for complete search history.

(56) References Cited

U.S. PATENT DOCUMENTS

2010/0221366 A1* 9/2010 Pan ................................ 424/750

OTHER PUBLICATIONS

Lee et al. Appl Microbiol Biotechnol. 2006, 72:1254-1262.*
Lee et al. J. Agric. Food Chem., 2007, 55 (16), pp. 6493-6502.*

* cited by examiner

*Primary Examiner* — Christian Fronda
(74) *Attorney, Agent, or Firm* — Anova Law Group, PLLC

(57) ABSTRACT

The present invention relates to a mutant of *Monascus purpureus* NTU 568, a nucleotide sequence for *Monascus purpureus* NTU 568 and primers for nucleotide sequence of *Monascus purpureus* NTU 568, wherein the *Monascus purpureus* NTU 568 having the nucleotide sequence of SEQ ID NO 1, SEQ ID NO 2 or SEQ ID NO 3 is deposited with Deutsche Sammlung von Mikroorganismen and Zellkulturen GmbH (DSMZ, Inhoffenstr. 7B, D-38124 Braunschweig, Germany) on Nov. 18, 2013, with the accession number of DSM 28072. Moreover, the nucleotide sequence for NTU 568 and the primers for the nucleotide sequence are proposed in order to facilitate the person skilled in *Monascus purpureus* filed capable of carrying out the strain (mutant) identification of the NTU 568 according to the present invention. Moreover, the person skilled in *Monascus purpureus* filed can also rapidly complete the strain (mutant) identification of the NUT 568 by using DNA molecular marker technology, without culturing any isolated *Monascus purpureus* strain or live *Monascus purpureus* bacteria.

2 Claims, 5 Drawing Sheets

SEQUENCE LISTING

<160> NUMBER OF SEQ ID NOS: 9

<210> SEQ ID NO 1
<211> LENGTH: 1389
<212> TYPE: DNA
<213> ORGANISM: Monascus purpureus
<220> FEATURE:

<400> SEQUENCE: 1

```
gactgcggtc atccggccca ggaaaccaga atggatatct ggcgccttct         50
agaacctgga tagtggccgg atccctcgcg ctgggagcct gggtgactat        100
gagggaggcg ttggaaccgg aggcgccata attattgatg agggccgcgc        150
ggaagtcctc gttccagggc gtcagcttgg tggcaatctt catgttatgt        200
tctggcaagg cttttatgga tggattcatg gtggtaaagc ttgcctgggg        250
tgggatgtaa ccttcattaa tcatgaggag caccttgatg agggaaatga        300
cccctgacgt acactcggta tgtccgatga ggcccttgac agagccaaag        350
tgcagtggtg ttgagcgatt ggggccccca agtactctca ggatactctc        400
atattctgct gggtctccca caggagtgcc agtgccgtga gcttcaacga        450
cagtaatctg tttaggcacc agatgggcct ccctggtaac gtccttgaag        500
agctctgaaa gggagggcga gtttggcacg aagattgggg tgcagttctg        550
gttttgatag acagcggtgc tcgcaatggt ccccaggatc tggtcgccgt        600
cctcaattgc agtgctgagc ttcttcaaga agacagcagc aatgccttca        650
ccgcgacaat agccatctgc atgagcgtcg aatggcttgc attggcccgt        700
tggactcagg aaggacgccc ctgccaagtt ctggaaccag agaggattcg        750
tcattacatt cgtaccaccg gccagggcag cggtacactc gccgctgagg        800
atagctttgc aggcctgatg aactgctaca gcggacgagg agcatgcagt        850
gtcgatggtc aggccaggac cggtccagcc gaagtagtgg ctgatctttc        900
ctgcaatgaa gctcttcagg ttgccagtgg ccgagaaggc attcggagca        950
tggcaggcaa tgttgttctc atagtccgca gcgcaaacgc caatatagca       1000
cccaatctgc ttgtcaacgc tggggttgca gaaatatccc gactgttcga       1050
cagcctgata ggcgatttgc agcatgtggc gctgctgagg atccgtcgag       1100
gcaatctctc gcgggctctt cttgaagaac ttgtgatcaa aggcatcgtg       1150
gtctcggata aagtttccaa accacttccg tttcgtatcg agctcgcgga       1200
atattgtgtc gaaggtaaag cgttccttgg gtacttcctg gtgctgtgac       1250
tcccccctgc agagcaagtc ccagaaccct tcgaggtcat ctgcaccggc       1300
caccttacac gacatgccaa tgacggcgat gtcgttttcg tcgaccgcat       1350
gggcgtattt caaagcagat gtagctccgg ggacacgca                   1389
```

<210> SEQ ID NO 2
<211> LENGTH: 1024
<212> TYPE: DNA
<213> ORGANISM: Monascus purpureus
<220> FEATURE:

<400> SEQUENCE: 2

| | | | | |
|---|---|---|---|---|
| gcgagccaac | cgtctggacc | aactcgaccg | tcattctctc | aaagtcctga | 50 |
| cggatctgcc | ctcctatccc | tggatgcatt | ccctccggtt | ctggtacgag | 100 |
| tctcgtctaa | gctatgacta | tcgccatcga | tcacaccctc | gtcaccacct | 150 |
| ggtaggggct | cccacggcgg | atcacaacgc | actggagccg | agatggagaa | 200 |
| actacctgcg | ggtctccgag | agcccctgga | tacgcgagca | cgtcgttcag | 250 |
| tctcgcataa | tctacccagg | tgcgggattc | atcgtgatgg | caatcgaggc | 300 |
| tgccgctcag | ctggcggatt | cgtcgaagaa | ggtcaagggg | ttcgagctgc | 350 |
| gagatgtcca | gatcaaccgg | gcattgcagg | tgccggaagg | cgaagaaggc | 400 |
| gttgaaacca | tactccacct | gcgtccgtat | caggcgcagg | gcctcaccaa | 450 |
| gggctcgcac | tgggacgagt | tcgtcatcta | ttcctaccag | tcaacgcagg | 500 |
| gctggcaaga | ccacgcgcgt | ggcttgatcg | tgacacacta | ccacagcaac | 550 |
| aaggcggggt | ttgatctgca | tcgggaagac | gagatacagc | tgcagatgca | 600 |
| tcggagcaa | tacctgagat | cctctgggct | atgcttgtcg | acaatcgaac | 650 |
| tggatgcgtt | ctacgatcgc | ctcggccaga | tgggcatgga | atttggtccg | 700 |
| gcattccgca | acctgtcgag | catccgacac | tgcaacggcc | agagtgtctg | 750 |
| tcagctgcgt | attccagaca | ccaaagtgca | gatgccagac | gagtttgagt | 800 |
| ttaagcatgt | tattcacccc | atcacgctgg | ataacatctt | ccacatggtt | 850 |
| ctgccctctc | gagtaggatc | gggtgcatcg | atgagggatg | cgcatgttcc | 900 |
| ggtctccctg | cagagtctgt | atattgctgc | cgatataaaa | agcaaccctg | 950 |
| ggaccctcct | tacaggccaa | tccaccatta | cgcatgagga | cgacagcggt | 1000 |
| tttggggcaa | cggtggtcgt | ctcg | | | 1024 |

<210> SEQ ID NO 3
<211> LENGTH: 1296
<212> TYPE: DNA
<213> ORGANISM: Monascus purpureus
<220> FEATURE:

<400> SEQUENCE: 3

| | | | | |
|---|---|---|---|---|
| agcacctcgg | agcaacggtt | cttgcgattg | caaatacaat | gagtgggaaa | 50 |
| ctgagcttgc | tcaattcctt | cccggattca | actgttctca | ccctggatga | 100 |
| aattacgaat | tcgagcactc | agacgttcgg | acgagcggac | gtcatcctga | 150 |
| gcaaccatgg | ggtcaaccca | agatggtatc | atggggaatt | attagggcca | 200 |
| tgcgggcgct | ttatcgatta | ctctgacatt | gaaggtacca | cgagtcatat | 250 |
| tgcagatgac | agtcaggctg | atgaaatctt | gatccatagc | gaagtctgtg | 300 |
| ccaggattga | cctcgactgt | cttctcaagc | atcgaccagt | gctggtttct | 350 |
| gaagtcttag | aagtcgcgca | caatttggtt | agagagagaa | tcgtgaatat | 400 |
| tggaggcaaa | gagcccaaga | tattctcatt | ctcacaacta | caacttgcat | 450 |
| ttgaccacct | ggcatctatg | caggacactg | tgcctactat | catcacggcc | 500 |
| gaagacggct | gtcaagtcag | cgtctcgcca | ccatccttcg | gctccacccc | 550 |
| attcatcttc | tccccggaca | aagtgtatct | tctcgtgggg | ggcctgagcg | 600 |
| gtcttggcct | tgagctggcc | gaatggatgg | tgctccgtgg | cgcgcgtcag | 650 |

```
cttgctttca tgtctcgatc gggtgcagga aacgccgctg cgactgctat          700
gctggcgaga ttggcggcaa aaggggcgcg aacaacggtg taccgatgcg          750
atgtgaccga tttctccgca gtgggacaat gcatcatgca gatagggcct          800
cagttaggcg gtattttcca tgccgctgcg gtgattgatg actgccccct          850
gcagcagatg tccgtttccc aatggtgtcg cacaatctcg cccaaggtcc          900
gcggagcaga caaccttgat cgagcaacag caggcatgga cttggacttt          950
ttcatctgct tctcctctgc ctcagcagtg gttggaacca aggcccaggc          1000
aagctatgtg gccggcaaca cctacatgga cgccctgatg cggagccgtc          1050
gacagcgcgg actaagtggc acggccatta atatcggcat ggtgataggg          1100
attggtctgg tcgctgcgga tgctaagctt gaggcaagca tgaaacggac          1150
tggtttcgat ccggtcaatg agtatgaatt cttctgtctg atagaagagg          1200
cagttcagac aggacgctcg ctgacgacct ccgacgacgg gaacatggag          1250
agtttccgga ttgttactgg ggctcgcgtg acagggccac agtgct              1296
```

```
<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotides

<400> SEQUENCE: 4
gactgcggtc atccggccc                                            19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotides

<400> SEQUENCE: 5
gcgtgtcccc ggagctaca                                            19

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 6
gcgagccaac cgtctggacc                                           20

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotides

<400> SEQUENCE: 7
gcgtgtcccc ggagctaca                                            19

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic oligonucleotides

<400> SEQUENCE: 8
gcgagccaac cgtctggacc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotides

<400> SEQUENCE: 9
cgagacgacc accgttgccc                                               20
```

MONASCUS PURPUREUS MUTANT, NUCLEOTIDE SEQUENCE FOR MONASCUS PURPUREUS MUTANT AND PRIMERS FOR NUCLEOTIDE SEQUENCE OF MONASCUS PURPUREUS MUTANT

CROSS-REFERENCE TO RELATED APPLICATION

This application is a continuation-in-part of U.S. application Ser. No. 12/946,823, filed on Nov. 15, 2010, the content of which is incorporated herein by reference in its entirety.

SEQUENCE LISTING

The instant application contains a Sequence Listing which has been submitted in ASCII format via EFS-Web and is hereby incorporated by reference in its entirety. The ASCII copy is named sequence.txt and is 5,746 bytes in size.

BACKGROUND OF THE INVENTION

1. Field of the Invention

The present invention relates to a *Monascus purpureus* mutant, and more particularly to a mutant of *Monascus purpureus* NTU 568, a nucleotide sequence for *Monascus purpureus* NTU 568 and primers for nucleotide sequence of *Monascus purpureus* NTU 568.

2. Description of the Prior Art

Recently, red yeast fermented products with multi functions are subject to more and more attention due to the flourishing development of health foods. In Asia, *Monascus purpureus* are applied in foods and medicines for thousands of years, wherein the secondary metabolites of *Monascus purpureus* can be divided into four kinds of:

(1) Pigment group: including the red pigment of rubropunctamine and monascorubramine, the yellow pigment of ankaflavin and monascin, and orange pigment of rubropunctanin and monascorubrin;
(2) Cholesterol-lowering substances: such as monacolin K;
(3) Hypotensive agent substances: such as γ-aminobutyric acid (GABA); and
(4) Antioxidant substances: including dimerumic acid and 3-hydoxy-4-methoxy-benzoic acid

*Monascus purpureus* NTU 568 is an excellent local *Monascus purpureus* strain, and which is studied and developed by Tzu-Ming PAN, the graduate chair of Institute of Microbiology and Biochemistry of National Taiwan University, and the R&D team thereof. Besides, currently, the healthcare characteristics of preventing Alzheimer's disease, hypolipidemic effect and antioxidative of the red mold (RM) powder manufactured by using the *Monascus purpureus* NTU 568 have been proven, wherein the health-care characteristics of preventing Alzheimer's disease, hypolipidemic effect and antioxidative of the RM powder is carried out by the secondary metabolites of monacolins, ankaflavin and monacsin.

Nowadays, the *Monascus purpureus* NTU 568 is successful to be commercialized. However, in spite of that, the strain (mutant) identification and the DNA molecular marker of the *Monascus purpureus* NTU 568 does still not be carried out, wherein the DNA molecular marker technology is usually used for identifying the DNA sequence or the RAPD genetic variation map.

Accordingly, in view of the specific DNA sequence, the specific RAPD genetic variation map, and the DNA molecular marker of the *Monascus purpureus* NTU 568 still does not be finished, the inventor of the present application has made great efforts to make inventive research thereon and eventually provided a mutant of *Monascus purpureus* NTU 568, a nucleotide sequence for *Monascus purpureus* NTU 568 and primers for nucleotide sequence of *Monascus purpureus* NTU 568.

SUMMARY OF THE INVENTION

The primary objective of the present invention is to provide a mutant of *Monascus purpureus* NTU 568, a nucleotide sequence for *Monascus purpureus* NTU 568 and primers for nucleotide sequence of *Monascus purpureus* NTU 568, therefore the person skilled in *Monascus purpureus* filed is able to carried out the strain (mutant) identification of the *Monascus purpureus* NTU 568 according to the present invention. Moreover, the person skilled in *Monascus purpureus* filed can also rapidly complete the strain (mutant) identification of the *Monascus purpureus* NTU 568 by using DNA molecular marker technology, without culturing any isolated *Monascus purpureus* strain or live *Monascus purpureus* bacteria.

Accordingly, to achieve the primary objective of the present invention, the inventor of the present invention provides a *Monascus purpureus* mutant, which is *Monascus purpureus* NTU 568 having a nucleotide sequence of SEQ ID NO 1, SEQ ID NO 2 or SEQ ID NO 3. The *Monascus purpureus* NTU 568 was deposited with Deutsche Sammlung von Mikroorganismen and Zellkulturen GmbH (DSMZ, Inhoffenstr. 7B, D-38124 Braunschweig, Germany) on Nov. 18, 2013, with the accession number of DSM 28072. Moreover, the nucleotide sequence of the *Monascus purpureus* NTU 568 can be formed by treating the RAPD (Random Amplification of Polymorphic DNA) and the PCR (Polymerase Chain Reaction) process to a plurality of specific primers, wherein the specific primers comprising a first nucleotide sequence of SEQ ID NO 4, a second nucleotide sequence of SEQ ID NO5, a third nucleotide sequence of SEQ ID NO6, a fourth nucleotide sequence of SEQ ID NO7, a fifth nucleotide sequence of SEQ ID NO8, and a sixth nucleotide sequence of SEQ ID NO9.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
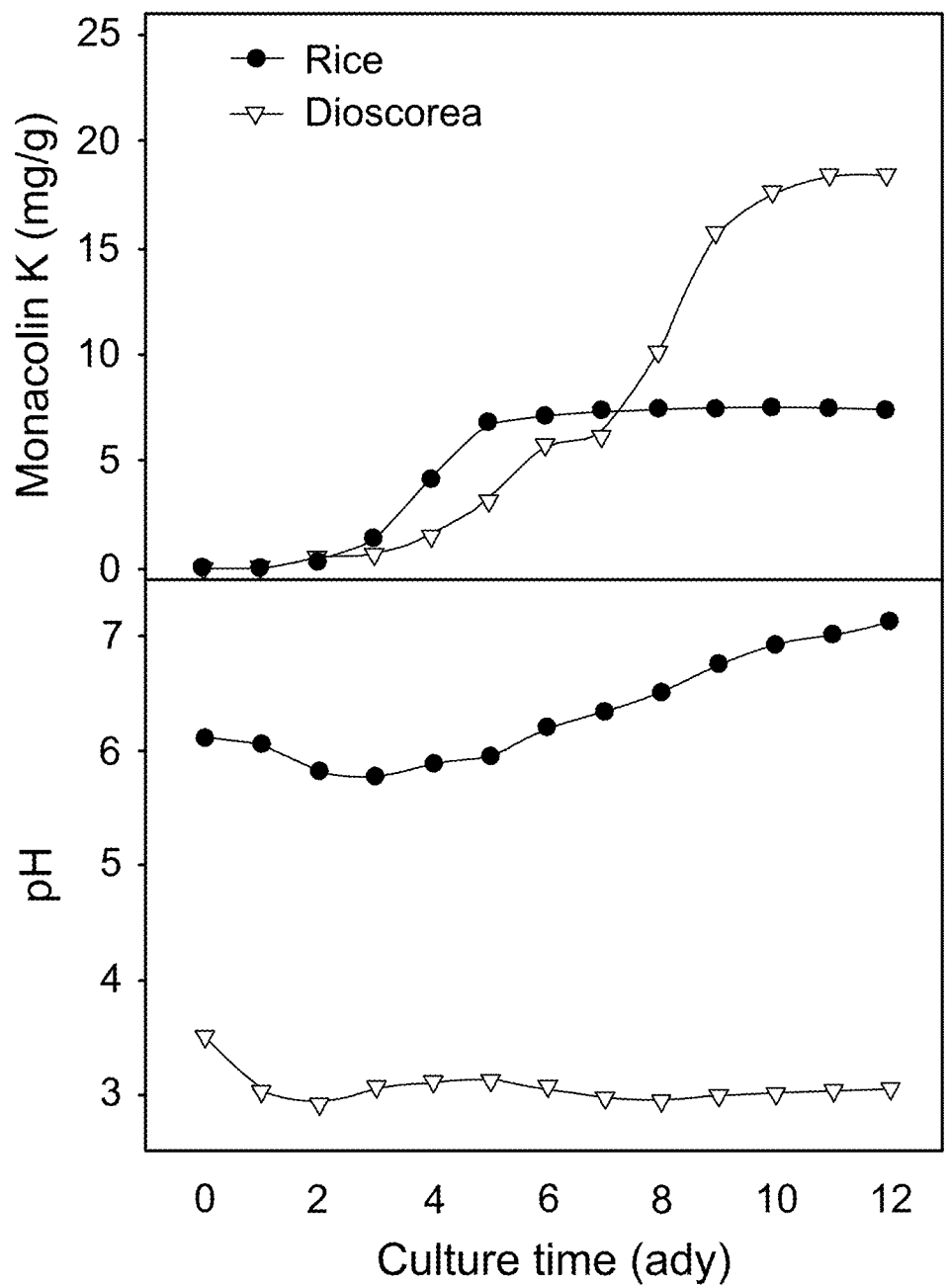
FIG. 1 is curve plots of time vs. monacolin K production and time vs. pH value for rice substrate and dioscorea substrate.

To more clearly describe a *Monascus purpureus* mutant, nucleotide sequences for the *Monascus purpureus* mutant and primers for the nucleotide sequences of the *Monascus purpureus* mutant according to the present invention, embodiments of the present invention will be described in detail with reference to the attached drawings hereinafter.

Monascus purpureus NTU 568 is an excellent local Monascus purpureus strain, and which is studied and developed by Tzu-Ming PAN, the graduate chair of Institute of Microbiology and Biochemistry of National Taiwan University, and the R&D team thereof. In the present invention, the Monascus purpureus NTU 568 has a specific nucleotide sequence of SEQ ID NO 1, SEQ ID NO 2 or SEQ ID NO 3, and was deposited with Deutsche Sammlung von Mikroorganismen and Zellkulturen GmbH (DSMZ, Inhoffenstr. 7B, D-38124 Braunschweig, Germany) on Nov. 18, 2013, the accession number of the Monascus purpureus NTU 568 is DSM 28072. The Monascus purpureus NTU 568 includes the characteristics of: growing rapidly, strong starch hydrolysis, high metabolites production. The method for testing the viability of Monascus purpureus NTU 568 is the following: after transferring Monascus purpureus NTU 568 from a slant tube to a potato dextrose agar (PDA) for 5-day culture, digging 3 blocks of hyphal body with volume of 1 cm$^3$; and continuously, inoculating the hyphal body into a 100 mL medium containing 2% of rice powder, so as to culture the Monascus purpureus NTU 568 with shaking manner under 30° C. and 200 rpm for 48 hours; therefore, If the cultured liquid presents red color after 48 hours of culture, the viability of Monascus purpureus NTU 568 is well. The storage method for Monascus purpureus NTU 568 is to store on a PDA medium in a slant tube under 4° C., and then sub-culturing the Monascus purpureus NTU 568 every 3 months.

Moreover, for verifying the viability of Monascus purpureus NTU 568, it moves the strain of Monascus purpureus NTU 568 from a slant tube to a culture medium of potato dextrose agar (PDA) for culturing. After 15-day culture, it digs and takes out three mycelium with the size of 1 cm$^3$ from the PDA, and then disposes the three mycelium into a culture fluid having 2% rice powder for next-stage culture; therefore, after 48-hour culture, the Monascus purpureus NTU 568 reveals high viability because the culture fluid shows red color. Herein, it needs to further explain that, the storage method for Monascus purpureus NTU 568 is to culture the Monascus purpureus NTU 568 on a PDA medium disposed in a slant tube under the store temperature of 4° C.; moreover, the Monascus purpureus NTU 568 must be treated with one time sub-cultured per 3 months.

Next, in order to prove that the Monascus purpureus NTU 568 can indeed increase the production of monacolin K of the secondary metabolites, the various experiment results and data are presented as follows. Please refer to following table 1, which records the production of monacolin K extracted from fermented rice substrate and fermented dioscorea substrate which is fermented by using different Monascus purpureus species. According to table 1, it can find that the production of monacolin K extracted from the fermented substrate fermented by using Monascus purpureus NTU 568 is highest no matter the substrate is rice or dioscorea.

TABLE 1

| species of Monascus purpureus | Fermented substrate | Production amount of monacolin K (mg/g) |
|---|---|---|
| M. sp. CA 505 | rice | 2.42 |
|  | dioscorea | 8.45 |
| M. purpureus NTU 568 | rice | 7.62 |
|  | dioscorea | 18.92 |
| M. sp. CH 001 | rice | 5.92 |
|  | dioscorea | 17.65 |

TABLE 1-continued

| species of Monascus purpureus | Fermented substrate | Production amount of monacolin K (mg/g) |
|---|---|---|
| M. purpureus NTU 601 | rice | 0.58 |
|  | dioscorea | 3.54 |
| M. purpureus NTU 301 | rice | 0.51 |
|  | dioscorea | 3.08 |
| M. anka M13 | rice | 0.11 |
|  | dioscorea | 0.63 |
| M. sp. KT | rice | 0.36 |
|  | dioscorea | 3.89 |

Figure 2:
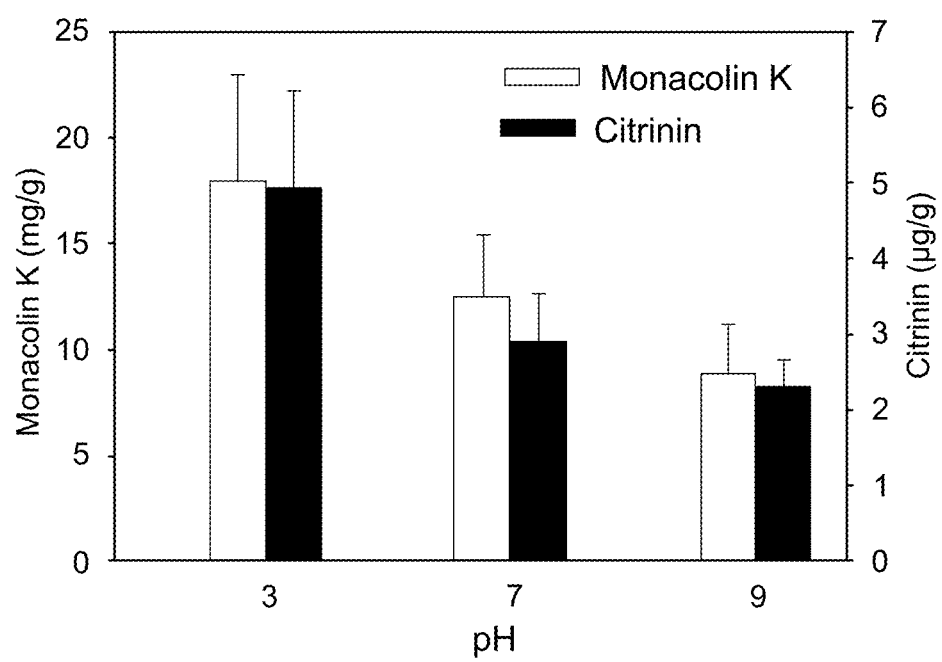
FIG. 2 is a bar graph of pH value vs. monacolin K production as well as citrinin production.

Please refer to FIG. 1, which illustrates curve plots of time vs. monacolin K production and time vs. pH value for rice substrate and dioscorea substrate. In FIG. 1, the solid circle data points represent the production of monacolin K extracted from the fermented rice substrate, and the hollow triangle data points mean the production of monacolin K extracted from the fermented dioscorea substrate. From FIG. 1, it can find that the pH value of the fermented dioscorea substrate reduces to 3.0 from 3.5 in 12-day culture and fermentation, and there has no obvious difference between the two pH values. Oppositely, the production of monacolin K extracted from the fermented dioscorea substrate is increased to 18 mg/g. In addition, please refer to FIG. 2, there is shown a bar graph of pH value vs. monacolin K production as well as citrinin production. From FIG. 2, it is able to know that there has no obvious difference between the monacolin K production and the citrinin production.

Next, in order to prove that the Monascus purpureus NTU 568 can indeed increase the production of monascin and ankaflavin of the secondary metabolites, the various experiment data are presented as follows. Please refer to following table 2, which records the production of monascin and ankaflavin extracted from different red mold fermented products. From table 2, it can apparently find that red mold fermented product fermented by using the Monascus purpureus NTU 568 includes the monascin of 11.65 mg/0.5 g and the ankaflavin of 1.77 mg/0.5 g, but others red mold fermented products does not includes monascin and ankaflavin.

TABLE 2

| Red mold species/products | Production amount of monascin (mg/0.5 g) | Production amount of ankaflavin (mg/0.5 g) |
|---|---|---|
| Monascus product (NU SKIN) | — | — |
| Monascus product (CPC) | — | — |
| Monascus product 1 (jensheng) | — | — |
| Monascus product (Koda) | — | — |
| Monascus product (Prince Pharmaceutical) | — | — |
| Monascus product (Standard) | — | — |
| Monascus product 2 (jensheng) | — | — |
| Monascus product 3 (jensheng) | — | — |
| Monascus product (SANHE) | — | — |
| Monascus product (YU-SHAN) | — | — |
| Monascus product (WEI-CHUAN) | — | — |
| Monascus purpureus NTU 568 | 11.65 | 1.77 |

Furthermore, in order to identify the DNA sequence of the Monascus purpureus NTU 568, it obtain the whole genome sequence of the *Monascus purpureus* NTU 568 by way of pyrosequencing, wherein the whole genome sequence of the *Monascus purpureus* NTU 568 includes 3,326 contigs with the total sequence length of 247,174,841 bps. Moreover, in the 3,326 contigs, the largest length of a specific contig is 175,588 bps.

Next, the *Aspergillus* is taken as a reference species and the software of FGENESH (SoftBerry, Inc., NY, USA) is then used for analyzing and predicting the DNA sequence of the *Monascus purpureus* NTU 568. The analysis and predict result shows 8,191 sequence data of mRNA and protein, wherein the total sequence length of the mRNA is 13,140,800 bps. Therefore, the whole genome sequence of the *Monascus purpureus* NTU 568 and the mRNA and protein sequence data are further edited to a single FASTA file, and then the FASTA file is transformed into a BLAST data by using the software of BLAST+ (Boratyn et al., 2013) for executing the gene search and alignment.

The gene search and alignment are executed by using polyketide synthases (PKSs) mechanism and model. Please refer to following table 3, which records several PKS fragments in PKS conserved domain. Therefore, the gene alignment between the PKS fragments of *M. pilosus* mokA and the BLASTp data of the *Monascus purpureus* NTU 568 as well as the BLASTn data of the *Monascus purpureus* NTU 568 have been completed.

TABLE 3

| Accession no. | Description | Sequence |
| --- | --- | --- |
| cd00833 | a polyketide synthases (PKSs) polymerize simple fatty acids into a large variety of different products, called polyketides, by successive decarboxylating Claisen condensations. PKSs can be divided into 2 groups, modular type I PKSs consisting of one or more large multifunctional proteins and iterative type II PKSs, complexes of several monofunctional subunits. | IAIVGMACRFPGAADPDE FWENLLEGRDAISEIPEDRWDA DGYYPDPGKPGKTYTRRGGFL DDVDAFDAAFFGISPREAEAM DPQQRLLLEVAWEALEDAGYS PESLAGSRTGVFVGASSSDYLE LLARDPDEIDAYAATGTSRAFL ANRISYFFDLRGPSLTVDTACSS SLVALHLACQSLRSGECDLALV GGVNLILSPDMFVGFSKAGML SPDGRCRPFDADADGYVRGEG VGVVVLKRLSDALRDGDRIYA VIRGSAVNQDGRTKGITAPSGE AQAALIRRAYARAGVDPSDID YVEAHGTGTPLGDPIEVEALA KVFGGSRSADQPLLIGSVKSNI GHLEAAAGLAGLIKVVLALEH GVIPPNLHFETPNPKIDFEESPL RVPTEARPWPAPAGPRRAGVSS FGFGGTNAHVIL |
| DQ176595 | PKS domain sequence of polyketide synthase mokA of monacolin K biosynthetic gene cluster in *M. pilosus* | ACGACATCGTAGGGGGT GCGTTCGCGAGTCGCGATGAC CTCGGTCATCTTGGCGCTGCC AATCGAACCACTCTCCGCCTG GCCCTGCTTGTAATCGAAGAC CGCTTGGAACAAGGGGGCCG GTTCCGCTGTTTCGGCGGTGG CCCCCGGGACCTCGAATCCGA GGCGCTCGAGCAGCACCCCG TAGGGCACGCGGGCGTGCTG CATGGCCTCGCGCACCTTGTC CTTGGTGGCGACCAGGTGCTC GCCAAAGGTGATGTGCGGGA CGAAGTTGCGGAAGCGCAGC GGGAGCAGGTTGGCGAAAAA GCCCATGCCCGCCAGTTCATC CACGTTCGTGCGATTGGTGTC GGCCAGGCCTATGCTGAAGTC GCTGCTGCCCGTCAATCGTGC CAGGAGCACGTGGTACGCAG CCAGGTAGAATTGCATGGGCG TGGCTTTGTGCTTGCGACTGC GCTCGCGGATGCGGAAAGCG ACCATGGGGTCGAGACGCGC GATCGCTTCGTGTTGCTTCCA CGAGTTGGGCTGGCGGGCGT GGTTCGGGCTATTAAGGCCAT CTTCGCCCAGAAGCATCCGCG GGAGGACCGGGGACACCACG CCCGTGGGCTGGTGGTGCATC GATTCCCAGTACGCGAGGTCC GCATCCATCTGGCCGGACTCG AGCGCTTCTCGCTGCCGCGTC GCGAGGTCTGCAAATTGAGG GACGTGCTTGTCGAGGGTCA CGCCGCCGTATAACTGGCTCG CTTCGACAAAGATATT |

Therefore, the gene alignment results reveal that, besides the well-known PKS genomes of citrinin (Accession: AB243687.1), monacolin K (Accession: DQ176595.1) and PKS1 (Accession: AJ414729.1), the whole genome sequence of the *Monascus purpureus* NTU 568 further includes 7 candidate gene fragment in PKS conserved domain, wherein the 7 candidate gene fragment are named as PKSε, PKSθ, PKSγ, PKSκ, PKSδ, PKSα, and PKSσ recorded in following table 4. Moreover, after completing the DELTA-BLAST analysis, the PKS fragments of PKSγ, PKSδ and PKSα are regarded as new PKS fragments of *M. purpureus* which are never recorded or written in any literatures or data base.

TABLE 4

| PKS ID | Contig no. | Protein sequence ID | E value |
|---|---|---|---|
| PKSε | 986 | 148__exon_(s)_431197__-_443034__3945_aa,_chain_+ | 1e−102 |
| PKSθ | 195 | 1001__12_exon_(s)_2896331__-_2908604__3854_aa,_chain_+ | 1e−102 |
| PKSγ | 549 | 535__6_exon_(s)_1607184__-_1614486__2307_aa,_chain_- | 7e−98 |
| PKSκ | 1154 | 396__5_exon_(s)_1203158__-_1210134__2245_aa,_chain_+ | 6e−92 |
| PKSδ | 977 | 403__6_exon_(s)_1222398__-_1229259__2188_aa,_chain_+ | 7e−77 |
| PKSα | 657 | 38__6_exon_(s)_101837__-_106246__1263_aa,_chain_- | 9e−72 |
| PKSσ | 200 | 757__13_exon_(s)_2356480__-_2361939__1583_aa,_chain_- | 5e−59 |

Based above gene search and alignment results, it is able to assume that the gene fragment of PKSα may be a novel gene fragment (sequence) for the *Monascus purpureus* NTU 568. Therefore, as listed in the following Sequence Listing, the nucleotide sequence of PKSα is defined as SEQ ID NO 1, and the sequence length of the nucleotide sequence of SEQ ID NO 1 is 1,390 bps. Furthermore, the nucleotide sequence of PKSα is treated with a BLASTx sequence alignment, and the alignment results are recorded in following table 5.

TABLE 5

| Accession no. | Description | Max identity (%) | E value |
|---|---|---|---|
| XP_002149769 | PKS: *Talaromyces marneffei* ATCC 18224 | 64.2 | 0 |
| XP_002340038 | PKS: *Talaromyces stipitatus* ATCC 10500 | 63.2 | 0 |
| EFW23245 | PKS: *Coccidioides posadasii* str. Silveira | 60.5 | 0 |
| XP_003070229 | PKS: *Coccidioides posadasii* C735 delta SOWgp | 60.4 | 0 |
| EJB11047 | citrinin (PKS): *Coccidioides immitis* C735 RS | 60.3 | 0 |
| XP_001243185 | hypothetical protein (CIMG_07081): *Coccidioides immitis* RS | 60.3 | 0 |
| XP_002487778 | PKS: *Talaromyces stipitatus* ATCC 10500 | 59.3 | 0 |
| EOD53036 | putative polyketide synthase protein: *Neofusicoccum parvum* UCRNP2 | 57.8 | 0 |

TABLE 5-continued

| Accession no. | Description | Max identity (%) | E value |
|---|---|---|---|
| CAK40124 | unnamed protein product: *Aspergillus niger* | 58.8 | 0 |
| XP_001393501 | polyketide synthase: *Aspergillus niger* CBS 513.88 | 58.8 | 0 |

Figure 3:
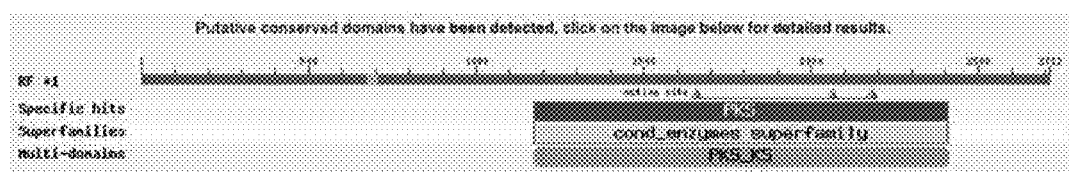
FIG. 3 is a conserved domain analysis diagram for PKSα nucleotide sequence.

Continuously, please refer to FIG. 3, there is shown a conserved domain analysis diagram for PKSα nucleotide sequence. From FIG. 3, it is able to know that the conserved domain PKS of PKSα is PKS_KS, which belongs to type II polyketide synthases (PKS). Moreover, from the table 5, it can further find that the PKS most similar to the PKSα is *Talaromyces marneffei* ATCC 1822 (identity=64.2), and there has no PKSs of *Monascus* genus similar or the same to the PKSα. So that, it is able to confirm that the gene fragment of PKSα is a novel gene fragment (sequence) for the *Monascus purpureus* NTU 568 based above comparison and analysis.

Moreover, the gene fragment of PKSδ can also be assumed as a novel gene fragment (sequence) for the *Monascus purpureus* NTU 568. As listed in the following Sequence Listing, the nucleotide sequence of PKSδ is defined as SEQ ID NO 2, and the sequence length of the nucleotide sequence of SEQ ID NO 2 is 1,024 bps. In order to identify whether the assumption is correct or not, the nucleotide sequence of PKSδ is treated with a BLASTx sequence alignment, and the alignment results are recorded in following table 6.

TABLE 6

| Accession no. | Description | Max identity (%) | E value |
|---|---|---|---|
| XP_001270321 | PKS: *Aspergillus clavatus* NRRL 1 | 80.1 | 0 |
| ENH62327 | Lovastatin nonaketide synthase: *Fusarium oxysporum* f. sp. cubense race 1 | 39.1 | 0 |
| EKV12048 | Phenolpthiocerol synthesis polyketide synthase ppsA: *Penicillium digitatum* PHI26 | 36.9 | 0 |
| ELA32194 | polyketide synthase: *Colletotrichum gloeosporioides* Nara gc5 | 36.5 | 0 |
| ELA38363 | polyketide synthase: *Colletotrichum gloeosporioides* Nara gc5 | 37.3 | 0 |
| EKV06858 | hypothetical protein PDIG_76310: *Penicillium digitatum* PH126 | 34.7 | 0 |
| EFQ35173 | containing protein: *Glomerella graminicola* M1.001 | 36.6 | 0 |
| XP_664395 | hypothetical protein AN6791.2: *Aspergillus nidulans* FGSC A4 | 34.3 | 0 |
| ENH88027 | polyketide synthase: *Colletotrichum orbiculare* MAFF 240422 | 37.1 | 0 |
| ELQ32864 | fatty acid synthase S-acetyltransferase: *Magnaporthe oryzae* Y34 | 37.8 | 0 |

Figure 4:
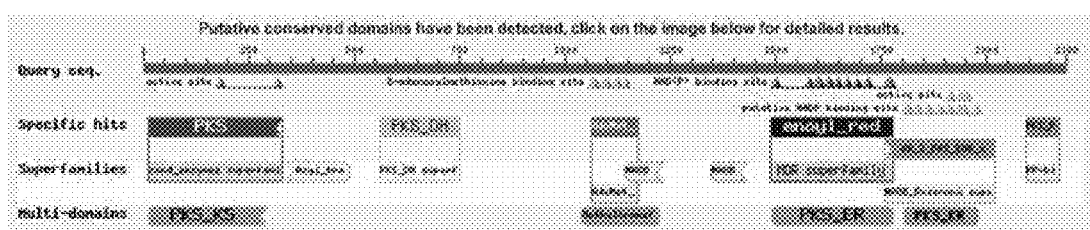
FIG. 4 is a conserved domain analysis diagram for PKSδ nucleotide sequence.

Please refer to FIG. 4, there is shown a conserved domain analysis diagram for PKSδ nucleotide sequence. From FIG. 4, it is able to know that the conserved domain PKS of PKSδ is PKS_KS-DH-MT-ER-KR-ACP, which belongs to type I polyketide synthases (PKS). Moreover, from the table 6, it can further find that the PKS most similar to the PKSδ is the polyketide synthases (PKS) of *Aspergillus clavatus* NRRL 1 (identity=80.1), and there has no PKSs of *Monascus* genus similar or the same to the PKSδ. So that, it is able to confirm that the gene fragment of PKSδ is a novel gene fragment (sequence) for the *Monascus purpureus* NTU 568 based above comparison and analysis.

Besides, the gene fragment of PKSγ can also be assumed as a novel gene fragment (sequence) for the *Monascus purpureus* NTU 568. As listed in the following Sequence Listing, the nucleotide sequence of PKSγ is defined as SEQ ID NO 3, and the sequence length of the nucleotide sequence of SEQ ID NO 3 is 1,096 bps. In order to identify whether the assumption is correct or not, the nucleotide sequence of PKSγ is treated with a BLASTx sequence alignment, and the alignment results are recorded in following table 7.

TABLE 7

| Accession no. | Description | Max identity (%) | E value |
|---|---|---|---|
| XP_002485355 | PKS: *Talaromyces stipitatus* ATCC 10500 | 44.8 | 0 |
| ADA79525 | PKS: *Delitschia winteri* | 44.9 | 0 |
| XP_001273762 | PKS: *Aspergillus clavatus* NRRL 1 | 45.1 | 0 |
| XP_002482833 | PKS: *Talaromyces stipitatus* ATCC 10500 | 44.4 | 0 |
| XP_001258783 | PKS: *Neosartorya fischeri* NRRL 181 | 45.5 | 0 |
| XP_001816573 | PKS: *Aspergillus oryzae* RIB40 | 44.8 | 0 |
| EDP53518 | PKS: *Aspergillus fumigatus* A1163 | 45.8 | 0 |
| XP_748462 | PKS: *Aspergillus fumigatus* Af293 | 45.6 | 0 |

TABLE 7-continued

| Accession no. | Description | Max identity (%) | E value |
|---|---|---|---|
| BAE54571 | unnamed protein product: *Aspergillus oryzae* RIB40 | 44.2 | 0 |
| XP_002383534 | PKS: *Aspergillus flavus* NRRL3357 | 44.3 | 0 |

Figure 5:
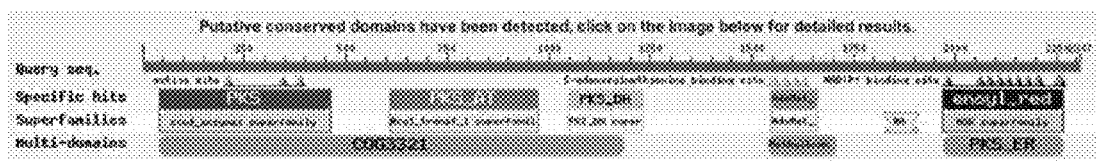
FIG. 5 is a conserved domain analysis diagram for PKSγ nucleotide sequence.

Please refer to FIG. 5, there is shown a conserved domain analysis diagram for PKSγ nucleotide sequence. From FIG. 5, it is able to know that the conserved domain PKS of PKSγ is PKS_KS-DH-MT-ER, which belongs to type I polyketide synthases (PKS). Moreover, from the table 7, it can further find that the PKS most similar to the PKSγ is the polyketide synthases (PKS) of *Talaromyces stipitatus* ATCC 10500 (identity=44.8), and there has no PKSs of *Monascus* genus similar or the same to the PKSγ. So that, it is able to confirm that the gene fragment of PKSγ is a novel gene fragment (sequence) for the *Monascus purpureus* NTU 568 based above comparison and analysis.

Thus, through above descriptions, the novel gene fragments and the related nucleotide sequence of the *Monascus purpureus* NTU 568 have been introduced. Next, for the nucleotide sequence of the *Monascus purpureus* NTU 568 can be formed by treating the RAPD (Random Amplification of Polymorphic DNA) and the PCR (Polymerase Chain Reaction) process to a plurality of specific primers, the specific primers will be introduced in follows.

As the following table 8 shows, the primers designed by the software of Geneious 4.5.8 are recorded. According to the following Sequence Listing, the nucleotide sequence of primer PKSα F is defined as SEQ ID NO 4 and has 19 bp sequence length, the nucleotide sequence of primer PKSα R is defined as SEQ ID NO 5 and has 19 bp sequence length, the nucleotide sequence of primer PKSδ F is defined as SEQ ID NO 6 and has 20 bp sequence length, and the nucleotide sequence of primer PKSδ R is defined as SEQ ID NO 7 and has 20 bp sequence length. Moreover, according to the following Sequence Listing, the nucleotide sequence of primer PKSγ F is defined as SEQ ID NO 8 and has 20 bp sequence length, and the nucleotide sequence of primer PKSγ R is defined as SEQ ID NO 9 and has 20 bp sequence length.

TABLE 8

| Primer ID | Sequence (5' → 3') | Target |
|---|---|---|
| PKSα F | A C T G C G G T C A T C C G G C C C | PKSα |
| PKSα R | C G T G T C C C C G G A G C T A C A | |
| PKSδ F | G C G A G C C A A C C G T C T G G A C C | PKSδ |
| PKSδ R | C G A G A C G A C C A C C G T T G C C C | |
| PKSγ F | G C G A G C C A A C C G T C T G G A C C | PKSγ |
| PKSγ R | C G A G A C G A C C A C C G T T G C C C | |

Continuously, the primers listed in the table 8 are executed RAPD through PCR process, wherein the polymerase chain reaction cocktail contains 3 ng DNA, 20 nM primers, a 1× Exsel reaction buffer, 0.5 U Exsel DNA polymerase (Bertec Enterprise, Taipei, Taiwan), and 100 M dNTPs. The reaction conditions of the PCR is as described: (1) 35-cycle processes with 95° C. (5 min) for heating, 95° C. (30 sec) for heating and −62° C. (1 min) for cooling; and (2) 70° C. (10 min) for reaction. Moreover, after completing the PCR process, it is able to execute the electrophoresis analysis for the PCR products by using 1% agarose gel, wherein the MISSION BIO-TECH Co. Ltd. is commissioned to complete the electrophoresis analysis. After electrophoresis analysis and genome sequencing, it is able to confirm and prove that the PKSα, PKSγ and PKSδ are indeed the novel gene fragment (sequence) for the *Monascus purpureus* NTU 568.

| PKS ID | Sequence Length (bp) | Sequence |
|---|---|---|
| α | 1390 | GACTGCGGTCATCCGGCCCAGGAAACCAG AATGGATATCTGGCGCCTTCTAGAACCTGG ATAGTGGCCGGATCCCTCGCGCTGGGAGC CTGGGTGACTATGAGGGAGGCGTTGGAA CCGGAGGCGCCATAATTATTGATGAGGGC CGCGCGGAAGTCCTCGTTCCAGGGCGTCA GCTTGGTGGCAATCTTTCATGTTATGTTCTG GCAAGGCTTTTATGGATGGATTCATGGTGG TAAAGCTTGCCTGGGGTGGGATGTAACCTT CATTAATCATGAGGAGCACCTTGATGAGGG AAATGACCCCTGACGTACACTCGGTATGTC CGATGAGGCCCTTGACAGAGCCAAAGTGC AGTGGTGTTGAGCGATTGGGGCCCCAAGT ACTCTCAGGATACTCTCATATTCTGCTGGGT CTCCCACAGGAGTGCCAGTGCCGTGAGCTT CAACGACAGTAATCTGTTTAGGCACCAGAT GGGCCTCCCTGGTAACGTCCTTGAAGAGCT CTGAAAGGGAGGGCGAGTTTGGCACGAAG ATTGGGGTGCAGTTCTGGTTTTGATAGACA GCGGTGCTCGCAATGGTCCCCAGGATCTGG TCGCCGTCCTCAATTGCAGTGCTGAGCTTC TTCAAGAAGACAGCAGCAATGCCTTCACC GCGACAATAGCCATCTGCATGAGCGTCGA ATGGCTTGCATTGGCCCGTTGGACTCAGGA AGGACGCCCTGCCAAGTTCTGGAACCAG AGAGGATTCGTCATTACATTCGTACCACCG GCCAGGGCAGCGGTACACTCGCCGCTGAG GATAGCTTTGCAGGCCTGATGAACTGCTA CAGCGGACGAGGAGCATGCAGTGTCGATG GTCAGGCCAGGACCGGTCCAGCCGAAGTA GTGGCTGATCTTTCCTGCAATGAAGCTCTT CAGGTTGCCAGTGGCCGAGAAGGCATTCTG GAGCATGGCAGGCAATGTTGTTCTCATAGT CCGCAGCGCAAACGCCAATATAGCACCCA ATCTGCTTGTCAACGCTGGGGTTGCAGAAA TATCCCGACTGTTCGACAGCCTGATAGGCGA TTTGCAGCATGTGGCGCTGCTGAGGATCCG TCGAGGCAATCTCTCGCGGGCTCTTCTTGA AGAACTTGTGATCAAAGGCATCGTGGTCTC GGATAAAGTTTCCAAACCACTTCCGTTTCG TATCGAGCTCGCGGAATATTGTGTCGAAGG TAAAGCGTTCCTTGGGTACTTCCTGGTGC TGTGACTCCCCCCTGCAGAGCAAGTCCCA GAACCCTTCGAGGTCATCTGCACCGGCCA CCTTACACGACATGCCAATGACGGCGATG TCGTTTTCGTCGACCGCATGGGCGTATTT CAAAGCAGATGTAGCTCCGGGGACACGCA |
| δ | 1024 | GCGAGCCAACCGTCTGGACCAACTCGACC GTCATTCTCTCAAAGTCCTGACGGATCTGC CCTCCTATCCCTGGATGCATTCCTCCGGTT CTGGTACGAGTCTCGTCTAAGCTATGACTAT CGCCATCGATCACACCCTCGTCACCACCTG GTAGGGGCTCCCACGGCGGATCACAACGCA CTGGAGCCGAGATGGAGAAACTACCTGCGG GTCTCCGAGAGCCCCTGGATACGCGAGCAC GTCGTTCAGTCTCGCATAATCTACCCAGGTG CGGGATTCATCGTCGATGGCAATCGAGGCTG CCGCTCAGCTGGCGGATTCGTCGAAGAAGG TCAAGGGGTTCGAGCTGCGAGATGTCCAGA TCAACCGGGCATTGCAGGTGCCGGAAGGCG AAGAAGGCGTTGAAACCATACTCCACCTGC GTCCGTATCAGGCGCAGGGCCTCACCAAGG GCTCGCACTGGGACGAGTTCGTCATCTATT CCTACCAGTCAACGCAGGGCTGGCAAGAC CACGCGCGTGGCTTGATCGTGACACACTA |

| PKS ID | Sequence Length (bp) | Sequence |
|---|---|---|
| | | CCACAGCAACAAGGCGGGGTTTGATCTGC<br>ATCGGGAAGACGAGATACAGCTGCAGATG<br>CATCGGGAGCAATACCTGAGATCCTCTGGG<br>CTATGCTTGTCGACAATCGAACTGGATGCG<br>TTCTACGATCGCCTCGGCCAGATGGGCATG<br>GAATTTGGTCCGGCATTCCGCAACCTGTCG<br>AGCATCCGACACTGCAACGGCCAGAGTGT<br>CTGTCAGCTGCGTATTCCAGACACCAAAG<br>TGCAGATGCCAGACGAGTTTGAGTTTAAG<br>CATGTTATTCACCCCATCACGCTGGATAAC<br>ATCTTCCACATGGTTCTGCCCTCTCGAGTA<br>GGATCGGGTGCATCGATGAGGGATGCGCA<br>TGTTCCGGTCTCCCTGCAGAGTCTGTATA<br>TTGCTGCCGATATAAAAAGCAACCCTGGG<br>ACCCTCCTTACAGGCCAATCCACCATTAC<br>GCATGAGGACGACAGCGGTTTTGGGGCA<br>ACGGTGGTCGTCTCG |
| γ | 1096 | AGCACCTCGGAGCAACGGTTCTTGCGATTG<br>CAAATACAATGAGTGGGAAACTGAGCTTGC<br>TCAATTCCTTCCCGGATTCAACTGTTCTCAC<br>CCTGGATGAAATTACGAATTCGAGCACTCA<br>GACGTTCGGACGAGCGGACGTCATCCTGAG<br>CAACCATGGGGTCAACCCAAGATGGTATCA<br>TGGGGAATTATTAGGGCCATGCGGGCGCTT<br>TATCGATTACTCTGACATTGAAGGTACCAC<br>GAGTCATATTGCAGATGACAGTCAGGCTGA<br>TGAAATCTTGATCCATAGCGAAGTCTGTGC<br>CAGGATTGACCTCGACTGTCTTCTCAAGCA<br>TCGACCAGTGCTGGTTTCTGAAGTCTTAGA<br>AGTCGCGCACAATTTGGTTAGAGAGAGAA<br>TCGTGAATATTGGAGGCAAAGAGCCCAAG<br>ATATTCTCATTCTCACAACTACAACTTGCA<br>TTTGACCACCTGGCATCTATGCGGACACT<br>GTGCCTACTATCATCACGGCCGAAGACGGC<br>TGTCAAGTCAGCGTCTCGCCACCATCCTTC<br>GGCTCCACCCCATTCATCTTCTCCCCGGAC<br>AAAGTGTATCTTCTCGTGGGGGGCCTGAGC<br>GGTCTTGGCCTTGAGCTGGCCGAATGGATG<br>GTGCTCCGTGGCGCGCGTCAGCTTGCTTTC<br>ATGTCTCGATCGGGTGCAGGAAACGCCGCT<br>GCGACTGCTATGCTGGCGAGATTGGCGGCA<br>AAAGGGGCGCGAACAACGGTGTACCGATG<br>CGATGTGACCGATTTCTCCGCAGTGGGACA<br>ATGCATCATGCAGATAGGGCCTCAGTTAGG<br>CGGTATTTTCCATGCCGCTGCGGTGATTGA<br>TGACTGCCCCCTGCAGCAGATGTCCGTTTC<br>CCAATGGTGTCGCACAATCTCGCCCAAGGT<br>CCGCGGAGCAGACAACCTTGATCGAGCAA<br>CAGCAGGCATGGACTTGGACTTTTTCATCT<br>GCTTCTCCTCTGCCTCAGCAGTGGTTGGAA<br>CCAAGGCCCAGGCAAGCTATGTGGCCGGC<br>AACACCTACATGGACGCCCTGATGCGGAG<br>CCGTCGACAGCGCGGACTAAGTGGCACGG<br>CCATTAATATCGGCATTGGTGATAGGGATTG<br>GTCTGGTCGCTGCGGATGCTAAGCTTGAG<br>GCAAGCATGAAACGGACTGGTTTCGATCC<br>GGTCAATGAGTATGAATTCTTCTGTCTGAT<br>AGAAGAGGCAGTTCAGACAGGACGCTCGC<br>TGACGACCTCCGACGACGGGAACATGGAG<br>AGTTTCCGGATTGTTACTGGGGCTCGCGTG<br>ACAGGGCCACAGTGCT |

Thus, through the descriptions, the mutant of *Monascus purpureus* NTU 568, nucleotide sequence for *Monascus purpureus* NTU 568 and primers for nucleotide sequence of *Monascus purpureus* NTU 568 of the present invention has been completely introduced and disclosed; in summary, the present invention has the following advantages:

In the present invention, the nucleotide sequence for *Monascus purpureus* NTU 568 and the primers for the nucleotide sequence are proposed in order to facilitate the person skilled in *Monascus purpureus* filed capable of carrying out the strain (mutant) identification of the *Monascus purpureus* NTU 568 according to the present invention. Moreover, the person skilled in *Monascus purpureus* filed can also rapidly complete the strain (mutant) identification of the *Monascus purpureus* NTU 568 by using DNA molecular marker technology, without culturing any isolated *Monascus purpureus* strain or live *Monascus purpureus* bacteria.

The above description is made on embodiments of the present invention. However, the embodiments are not intended to limit scope of the present invention, and all equivalent implementations or alterations within the spirit of the present invention still fall within the scope of the present invention.

---

What is claimed is:

1. A *Monascus Purpureus* mutant, which is a *Monascus purpureus* NTU 568 having a nucleotide sequence of SEQ ID NO 1, SEQ ID NO 2 or SEQ ID NO 3, and was deposited with Deutsche Sammlung von Mikroorganismen and Zellkulturen GmbH (DSMZ, Inhoffenstr. 7B, D-38124 Braunschweig, Germany) on Nov. 18, 2013, the accession number of the *Monascus purpureus* NTU 568 being DSM 28072;

wherein the method for testing the viability of *Monascus purpureus* NTU 568 is the following: after transferring *Monascus purpureus* NTU 568 from a slant tube to a potato dextrose agar (PDA) for 5-day culture, digging 3 blocks of hyphal body with volume of 1 cm$^3$; and continuously, inoculating the hyphal body into a 100 mL medium containing 2% of rice powder or dioscorea powder, so as to culture the *Monascus purpureus* NTU 568 with shaking manner under 30° C. and 200 rpm for 48 hours; therefore, If the cultured liquid presents red color after 48 hours of culture, the viability of *Monascus purpureus* NTU 568 is well;

wherein the storage method for *Monascus purpureus* NTU 568 is to store on a PDA medium in a slant tube under 4° C., and then sub-culturing the *Monascus purpureus* NTU 568 every 3 months;

wherein the nucleotide sequence of the *Monascus Purpureus* strain NTU 568 can be identified by using following primers:

```
(1) primer PKSα F:   GACTGCGGTCATCCGGCCC;     (SEQ ID NO 4)

(2) primer PKSα R:   GCGTGTCCCCGGAGCTACA;     (SEQ ID NO 5)

(3) primer PKSδ F:   GCGAGCCAACCGTCTGGACC;    (SEQ ID NO 6)

(4) primer PKSδ R:   GCGTGTCCCCGGAGCTACA;     (SEQ ID NO 7)

(5) primer PKSγ F:   GCGAGCCAACCGTCTGGACC;    (SEQ ID NO 8)
and (6) primer PKSγ R:   CGAGACGACCACCGTTGCCC;    (SEQ ID NO 9)
```

Wherein the primer PKSα F or PKSα R can be used for identifying the nucleotide sequence of SEQ ID NO 1 through RAPD (Random Amplification of Polymorphic DNA) technology, the primer PKSδ F or PKSδ R can be used for identifying the nucleotide sequence of SEQ ID NO 2 through RAPD technology, and the primer PKSγ F or PKSγ R can be used for identifying the nucleotide sequence of SEQ ID NO 3 through RAPD technology.

2. The *Monascus Purpureus* mutant of claim 1, wherein the *Monascus purpureus* NTU 568 can increase the production of monacolin K in the secondary metabolites thereof.

\* \* \* \* \*